US008991614B2

(12) United States Patent
Rose et al.

(10) Patent No.: US 8,991,614 B2
(45) Date of Patent: Mar. 31, 2015

(54) MICROFLUIDIC ULTRASONIC PARTICLE SEPARATORS WITH ENGINEERED NODE LOCATIONS AND GEOMETRIES

(71) Applicant: Lawrence Livermore National Security, LLC, Livermore, CA (US)

(72) Inventors: Klint A. Rose, Alviso, CA (US); Karl A. Fisher, Brentwood, CA (US); Douglas A. Wajda, Urbana, IL (US); Raymond P. Mariella, Jr., Danville, CA (US); Christopher Bailey, Oakland, CA (US); Dietrich Dehlinger, San Francisco, CA (US); Maxim Shusteff, Oakland, CA (US); Byoungsok Jung, Palo Alto, CA (US); Kevin D. Ness, San Mateo, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/246,981

(22) Filed: Apr. 7, 2014

(65) Prior Publication Data
US 2014/0216992 A1    Aug. 7, 2014

Related U.S. Application Data

(62) Division of application No. 13/571,640, filed on Aug. 10, 2012, now Pat. No. 8,727,129.

(60) Provisional application No. 61/524,020, filed on Aug. 16, 2011.

(51) Int. Cl.
*B03B 5/00* (2006.01)
*B01D 21/28* (2006.01)
(Continued)

(52) U.S. Cl.
CPC .............. *B01D 21/28* (2013.01); *B01D 21/283* (2013.01); *B01L 3/502761* (2013.01); *G01N 33/491* (2013.01); *G01N 33/48728* (2013.01); *B01D 2221/10* (2013.01); *B01L 2200/0636* (2013.01); *B01L 2200/0652* (2013.01);
(Continued)

(58) Field of Classification Search
USPC .................................. 209/454, 455, 457, 458
See application file for complete search history.

(56) References Cited

U.S. PATENT DOCUMENTS 6,332,541 B1 * 12/2001 Coakley et al. ................. 209/18
7,674,630 B2 * 3/2010 Siversson ...................... 436/177
(Continued)

OTHER PUBLICATIONS

Karl A. Fisher and Robin Miles, "Modeling the acoustic radiation force in microfluidic chambers (L)," J. Acoust. Soc. Am, 123 (4): 1862-1865 (2008).

(Continued)

*Primary Examiner* — David H Bollinger
(74) *Attorney, Agent, or Firm* — Eddie E. Scott

(57) ABSTRACT

An ultrasonic microfluidic system includes a separation channel for conveying a sample fluid containing small particles and large particles, flowing substantially parallel, adjacent to a recovery fluid, with which it is in contact. An acoustic transducer produces an ultrasound standing wave, that generates a pressure field having at least one node of minimum, pressure amplitude. An acoustic extension structure is located proximate to said separation channel for positioning said acoustic node off center in said acoustic area and concentrating the large particles in said recovery fluid stream.

3 Claims, 5 Drawing Sheets

(51) Int. Cl.
*B01L 3/00* (2006.01)
*G01N 33/49* (2006.01)
*G01N 33/487* (2006.01)

(52) U.S. Cl.
CPC . *B01L 2300/0816* (2013.01); *B01L 2300/0864* (2013.01); *B01L 2400/0439* (2013.01); *B01L 2400/0487* (2013.01)
USPC .......................... 209/455; 209/457; 209/458

(56) References Cited

U.S. PATENT DOCUMENTS 8,727,129 B2 * 5/2014 Rose et al. .................... 209/455
2010/0126922 A1 * 5/2010 Takahashi et al. ............ 210/201

OTHER PUBLICATIONS

A. Haake and J. Dual, "Micro-manipulation of small particles by node position control of an ultrasonic standing wave," Ultrasonics, 40 : 317-322 (2002).
Hawkes et al., "Filtration of bacteria and yeast by ultrasound-enhanced sedimentation," J. of Applied Microbiology, 82: 39-47 (1997).
Glynne-Jones et al., "Multi-modal particle manipulator to enhance bead-based bioassays," Ultrasonics, 50: 235-239 (2010).
Jung et al., "Acoustic Particle Filter with Adjustable Effective Pore Size for Automated Sample Preparation," Anal. Chem., 80: 8447-8452 (2008).
Laurell et al., "Chip integrated strategies for acoustic separation and manipulation of cells and particles," Chem. Soc. Rev., 36: 492-506 (2007).

* cited by examiner

MICROFLUIDIC ULTRASONIC PARTICLE SEPARATORS WITH ENGINEERED NODE LOCATIONS AND GEOMETRIES

CROSS-REFERENCE TO RELATED APPLICATIONS

The present application is a divisional of pending U.S. application Ser. No. 13/571,640 filed Aug. 10, 2012, which is a non-provisional application of U.S. Provisional Patent Application No. 61/524,020 filed Aug. 16, 2011, the entire contents and disclosures of which are specifically incorporated by reference herein.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to microfluidic particle separators and more particularly to microfluidic ultrasonic particle separators with engineered node locations and geometries.

2. State of Technology

The article, "Chip integrated strategies for acoustic separation and manipulation of cells and particles," by Thomas Laurell, Filip Petersson, and Andreas Nilsson in *Chem. Soc. Rev.*, 2007, 36, 492-506, states: "Chip integrated strategies for acoustic separation and manipulation of cells and particles," by Thomas Laurell." The article includes the state of technology information quoted below and drawing FIGS. 1A, 1B, and 1C are copies of FIGS. 5, 6 and 7 from the article. The article, "Chip integrated strategies for acoustic separation and manipulation of cells and particles," by Thomas Laurell, Filip Petersson and Andreas Nilsson in *Chem. Soc. Rev.*, 2007, 36, 492-506, is incorporated herein in its entirety for all purposes.

"FIG. 5 Schematic cross-section of separation chip utilizing the Lund method. The silicon separation channel is sealed by a boron silica glass lid and is actuated from below using a piezoelectric ceramic." [FIG. 1A]

"FIG. 6 Illustrated cross-section (along the dashed line in FIG. 7) of a separation channel showing negative w-factor particles (e.g. lipid particles) collected in the pressure antinodes by the side walls and positive w-factor particles (i.e. red blood cells) in the pressure node." [FIG. 1B]

"FIG. 7 Illustration of separation of negative w-factor particles (black—centre outlet) and positive w-factor particles (grey—side outlets) in 45 u design chip." [FIG. 1C]

"The Lund-method for acoustic separation of suspended particles from their medium is based on a laminar flow microchannel that is ultrasonically actuated from below, using a piezoelectric ceramic (FIG. 5). The width of the channel is chosen to correspond to half the ultrasonic wavelength, thereby creating a resonator between the side walls of the flow channel in which a standing wave can be formed. The induced standing wave is thus generated orthogonal to the incident ultrasonic wave front. As suspended particles with a positive w-factor perfuse the channel they are moved, by means of the axial PRF, towards the pressure nodal plane along the channel centre, while those with a negative w-factor are moved towards the anti-nodal planes close to the side walls (FIG. 6)."

"The end of the separation channel is split into three outlet channels, thus allowing the positive w-factor particles to exit through the centre outlet and the negative w-factor particles to exit through the side outlets, provided that all outlet flow rates are alike (FIG. 7). The separation efficiency of positive and negative w-factor particles is defined as the fraction of particles exiting through the centre and side outlets respectively."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives failing within the spirit and scope of the invention as defined by the claims.

The present invention provides high-throughput sample processing of biological material. The system of the present invention separates out cell-sized particles from a background solution containing other biological materials (viruses, proteins nucleic acids, etc.) in order to allow uncontaminated analysis of either the background sample or the separated cells. The present invention uses the vibrations of a piezoelectric transducer to produce acoustic radiation forces within microfluidic channels. Whereas other investigators have demonstrated technologies that position a single stream of concentrated particles on the center-line of a fluid channel, or multiple streams of particles, such that some of them are off-center, the system of the present invention positions a single stream of concentrated particles off-center in the fluid channel. This is highly advantageous for achieving improved separation between the two sample fractions, and greater purity within each fraction. In one embodiment, the stream of concentrated particles is positioned off-center in the separation channel by means of subdividing the channel with one or more thin acoustically transparent walls. In another embodiment the stream of concentrated particles is positioned off-center n the fluid flow with the aid of a polymer gel structure positioned adjacent to the fluid channel. In these embodiments, or in any other, the pressure field resulting from the acoustic waves can be optimized by driving the piezoelectric transducer at multiple frequencies on a single device. Additionally, in these embodiments, or in any other, the separation channel can be routed in a serpentine fashion to pass multiple times (3, 5, etc.) through the ultrasound region, thereby providing a longer residence time for the sample in the acoustic field, increasing separation efficiency.

The present invention provides an ultrasonic microfluidic system for separating smaller particles from larger particles suspended in a sample fluid. This sample fluid flows down a separation channel, side-by-side with a "recovery buffer," which is typically a fluid into which the larger particles of interest are to be transferred. The two fluid streams are in contact with each other, but mixing is limited only to diffusion due to the low Reynolds number of microfluidic flows. An acoustic transducer in contact with the microfluidic chip produces an ultrasound pressure field throughout these fluids. Properly tuned to match the geometric parameters of the channel, the acoustic transducer generates a resonant standing wave within the fluid, creating one or more zones of minimal pressure amplitude (acoustic nodes) toward which particles are driven. The forces that particles experience are dependent on particle, size; therefore, the largest particles move toward the node fastest. Positioning the node within the recovery fluid stream allows the largest particles to be carried out of the chip with the recovery fluid, separating them from other sample components that remain in the sample stream. In one embodiment a second fluid channel ("bypass channel") is located substantially parallel to the separation channel. A wall that is thin enough to negligibly effect the transmission of ultrasound between the bypass and separation channel ("acoustically transparent wall") is located between the two channels. In another embodiment the stream of concentrated particles is positioned off-center in the fluid channel by means of a gel positioned adjacent the fluid channel.

The present invention enables improved operation of the acoustic separation module within the context of a Microfluidic Sample Preparation Platform that aims to purify, separate, and fractionate different classes of particles (mammalian and bacterial cells, nucleic acids, viruses, etc.) from complex biological samples for both clinical (blood, urine, saliva, etc.) and environmental analysis (food, water, aerosol, etc.). These analyses have obvious applications in areas such as biothreat detection, pathogen identification, epidemic monitoring, virology, and vaccine production, among others. The present invention can be used on its own or in conjunction with other sample processing steps to prepare biological samples before they are introduced into a great variety of commercial instruments for manipulating or analyzing biological samples, such as DNA sequencing, PCR, flow cytometry, microorganism detection, etc.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1A:
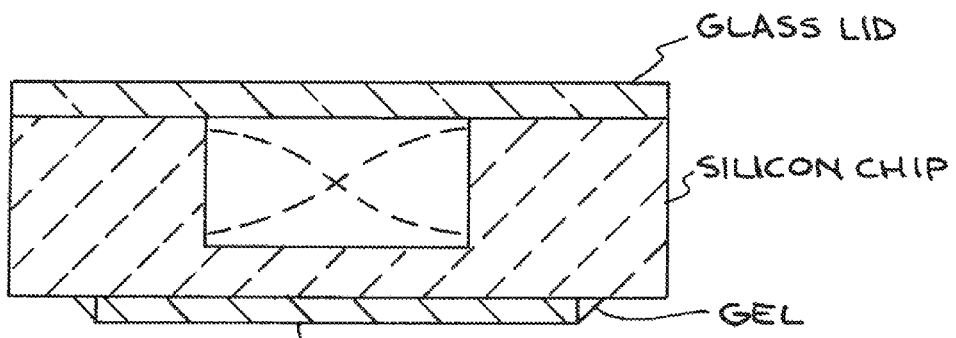
FIGS. 1A, 1B, and 1C (PRIOR ART) are copies of FIGS. 5, 6 and 7 from the article, "Chip integrated strategies for acoustic separation and manipulation of cells and particles," by Thomas Laurell, Filip Petersson; and Andreas Nilsson in Chem. Soc. Rev., 2007, 36, 492-506.
Figure 1B:
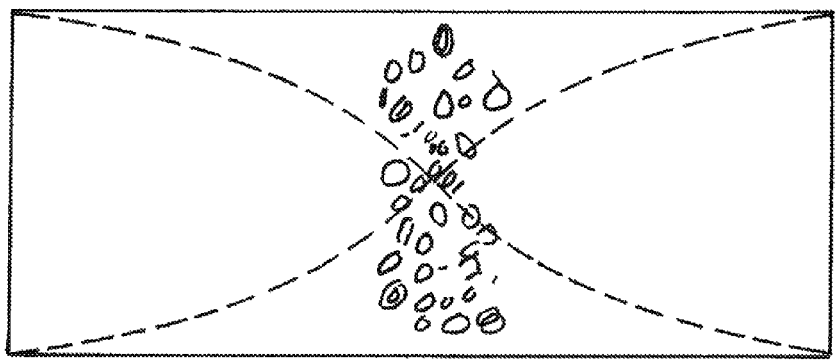
Figure 1C:
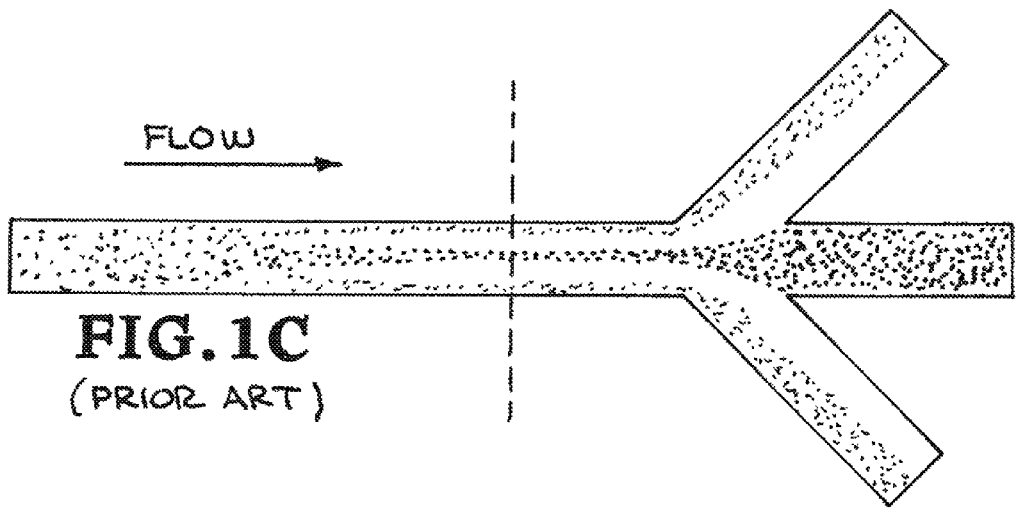

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention concerns the use of ultrasound to manipulate particles for the purposes of separating, preparing and analyzing clinical or environmental samples containing mixtures of biological particles (spores, cells, bacteria, viruses, molecules, etc.). In particular, when implemented within a fieldable, automated, continuous-flow system, the acoustical device is used to concentrate and filter out the largest particles. The device is highly robust and minimally sensitive to parameter variation to interface with downstream assays or other separation elements. The present invention can be used on its own or in conjunction with other sample processing steps to prepare biological samples before they are introduced into a great variety of commercial instruments for manipulating or analyzing biological samples, such as DNA sequencing, PCR, flow cytometry, microorganism detection, etc.

An ultrasonic particle manipulation in microfluidic device is realized using a piezoelectric transducer to generate acoustic standing waves within a microchannel. The primary acoustic radiation forces induced by the sound waves direct particles toward the pressure-field minima (nodes) or maxima (antinodes), depending on the relative compressibility and density between the particle and the suspending liquid. In general, if the radiation forces (which scale with particle volume) are directed transversely to the fluid flow direction, the induced motions are sufficient to achieve continuous, high-throughput separation for particles of diameter greater than about 2 micrometers.

Example 1

Single Node System

Figure 2A:
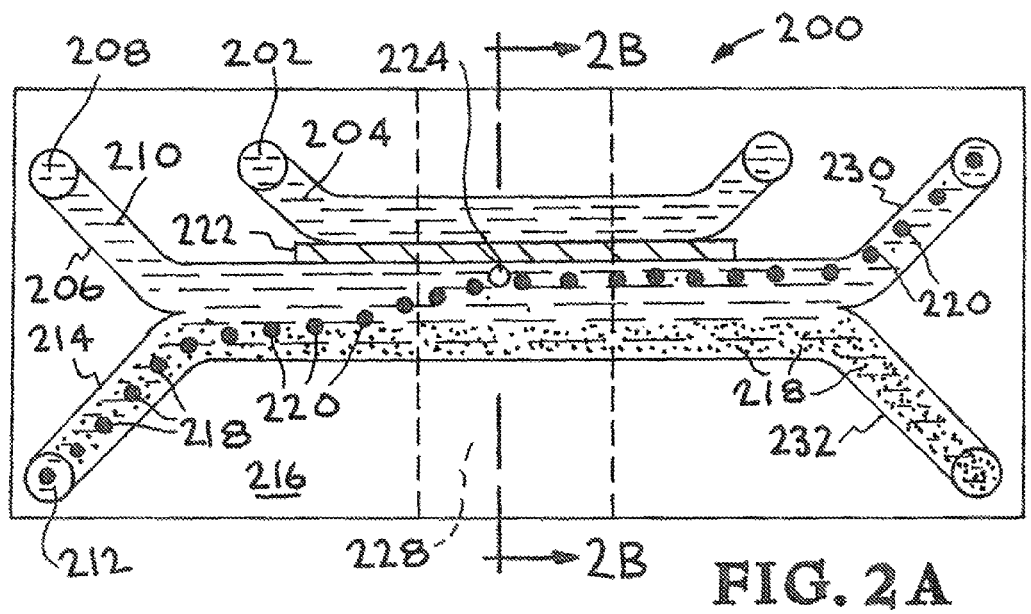
FIGS. 2A and 2B illustrate an embodiment of the invention wherein a transducer produces a single node.

Referring now to the drawings and in particular to FIG. 2A, one embodiment of the present invention is illustrated.

The device uses multiple microfluidic channels running in parallel along the length of a microfluidic chip, separated by specifically-designed distances (the "wall thickness"). One of these multiple channels serves as the separation channel and has two inlets and two outlets. The ultrasound standing-wave pressure fields are optimized to transfer focused particles out of the sample stream and into the recovery fluid within the recovery fluid channel. The piezoelectric transducer may be driven at single or multiple frequencies to achieve the optimal node placement depending on the channel and wall geometry. In addition, multiple small piezoelectric transducers may be arranged to produce different sound fields in different regions of the chip.

The present invention provides an ultrasonic microfluidic system for separating smaller particles from larger particles suspended in a sample fluid. This sample fluid flows down a separation channel, side-by-side with a "recovery buffer," which is typically a fluid into which the larger particles of interest are to be transferred. The two fluid streams are in contact with each other, but mixing is limited only to diffusion due to the low Reynolds number of microfluidic flows. An acoustic transducer in contact with the microfluidic chip produces an ultrasound pressure field throughout these fluids. Properly tuned to match the geometric parameters of the channel, the acoustic transducer generates a resonant standing wave within the fluid, creating one or more zones of minimal pressure amplitude (acoustic nodes) toward which particles are driven. The forces that particles experience are dependent on particle size; therefore, the largest particles move toward the node fastest. Positioning the node within the recovery fluid stream allows the largest particles to be carried out of the chip with the recovery fluid, separating them from other sample components that remain in the sample stream. In one embodiment a second fluid channel ("bypass channel") is located substantially parallel to the separation channel. A wall that is thin enough to negligibly effect the transmission of ultrasound between the bypass and separation channel ("acoustically transparent wall") is located between the two channels. In another embodiment the stream of concentrated particles is positioned off-center in the fluid channel by means of a gel positioned adjacent the fluid channel.

The embodiment illustrated in FIG. 2A is designated generally by the reference numeral 200. The device 200 has an "H-filter" geometry in which two fluids are pumped side-by-side down a microfluidic separation channel with two inlets and two outlets. One of the two fluids contains the sample 212, and the other fluid is a "recovery" buffer 208, which is an appropriate medium (water or buffer) into which focused particles are transferred, while the unfocused components remain in the sample and continue straight through the system. Channel depth (typically 100-300 micrometers), width (typ. 300-1000 micrometers), and wall thickness (typ. 10-40 micrometers) are determined for each chip based on the desired acoustic pressure fields, and fabricated by means of standard photolithography with anisotropic etching. The two fluids enter the separation channel through separate inlets, and the separated sample fractions are collected at the two outlets.

The present invention provides an ultrasonic microfluidic apparatus for separating small particles 218 from large particles 220 contained in the sample fluid 212. A sample input channel 214 is provided for conveying the sample fluid 212 containing small particles 218 and large particles 220 toward the separation area. A recovery fluid input channel 206 containing recovery fluid 208 is routed to convey the recovery fluid substantially parallel and adjacent the sample fluid. Within the separation channel, the recovery fluid contacts the sample fluid 212. A bypass fluid channel 204 containing bypass fluid 202 is located substantially parallel and adjacent the separation channel 206. An acoustically transparent wall 222 is located between the bypass channel 204 and the separation channel 206. The bypass channel 204 together with the wall 222 comprise an acoustic extension structure.

An acoustic transducer 228 in contact with the microfluidic chip 216 produces an ultrasound pressure field throughout the fluids 202, 208, and 212. Properly tuned to match the geometric parameters of the channel, the acoustic transducer 228 generates a resonant standing wave within the fluids 202, 208, and 212; creating one or more zones of minimal pressure amplitude (acoustic nodes) toward which particles are driven. The forces that particles experience are dependent on particle size; therefore, the largest particles 220 move toward the node 224 fastest. Positioning the node 224 within the recovery fluid 208 stream allows the largest particles 220 to be carried out of the chip 216 with the recovery fluid 208, separating them from other sample components that remain in the sample 212 stream.

Figure 2B:
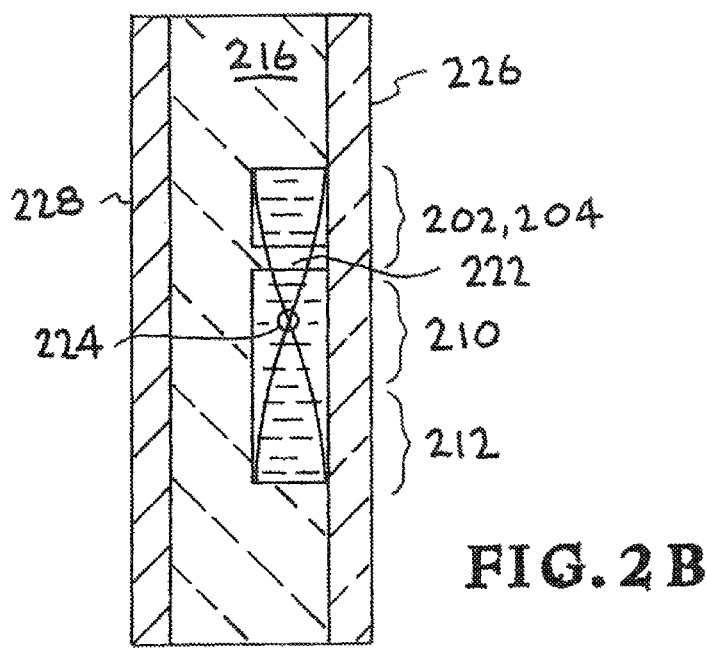

Referring now to FIG. 2B, a cross section taken along lines 28 of FIG. 2A in the direction of the arrows is shown. The body of the chip 216 includes a glass cover plate 226. The body of the chip 216 and the glass cover plate 226 enclose the bypass fluid channel 204, the bypass fluid 202, the recovery fluid 208, and the sample fluid 212. The acoustically transparent wall 222 maintains the bypass fluid 208 separate from the sample 212 and recovery fluid 208 in the separation channel.

The acoustic transducer 228 produces the single acoustic node 224, designed to lie within the recovery fluid 208 stream so that the recovery fluid 208 receives the large particles 220 that are concentrated at the acoustic node 224 causing them to be carried by the recovery fluid 208 out of the "large particle" outlet (LPO) 230.

Example 2

Two Node System

Figure 3A:
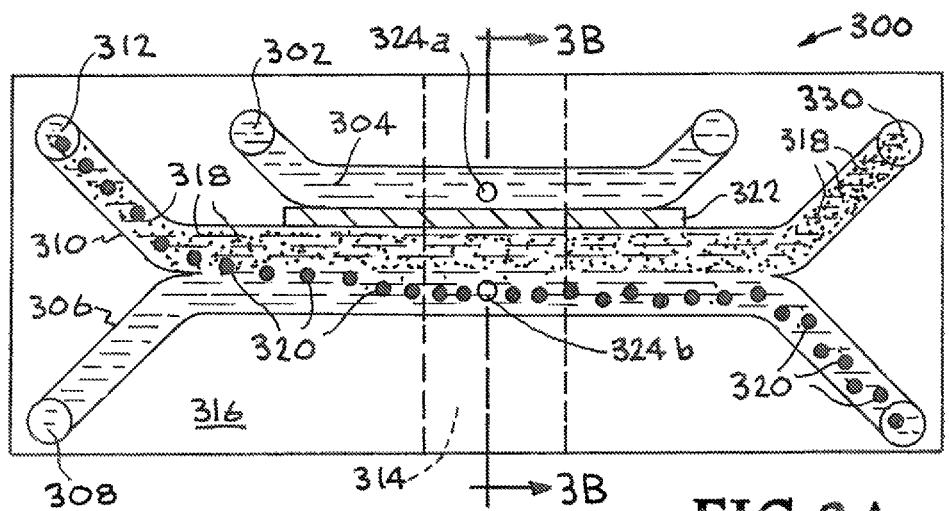
FIGS. 3A and 3B illustrate another embodiment of the invention wherein a transducer produces two nodes.

Referring now to FIG. 3A, another embodiment of the present invention is illustrated. The device uses multiple microfluidic channels running in parallel along the length of a microfluidic chip 316, separated by specifically-designed distances (the "wall thickness"). One of these multiple channels serves as the separation channel and has two inlets and two outlets. The ultrasound standing-wave pressure fields are optimized to transfer focused particles out of the sample stream and into the adjacent recovery fluid stream, which flow together down the separation channel. The piezoelectric transducer 314 may be driven at single or multiple frequencies to achieve the optimal node placement depending on the channel and wall geometry. In addition, multiple small piezoelectric transducers may be arranged to produce different sound fields in different regions of the chip.

The present invention provides an ultrasonic microfluidic system for separating smaller particles 318 from larger particles 326 suspended in a sample fluid 312. This sample fluid 312 flows down a separation channel 310, side-by-side with a "recovery buffer 308," which is typically a fluid into which the larger particles 326 of interest are to be transferred. The two fluid streams, 312 and 308, are in contact with each other, but mixing is limited only to diffusion due to the low Reynolds number of microfluidic flows. An acoustic transducer 314 in contact with the microfluidic chip 316 produces an ultrasound pressure field throughout these fluids. Properly tuned to match the geometric parameters of the channel, the acoustic transducer 314 generates a resonant standing wave within the fluid, creating one or more zones of minimal pressure amplitude (acoustic nodes) toward which particles are driven. The forces that particles experience are dependent on particle size; therefore, the largest particles 316 move toward the nodes 324b and 324a fastest. Positioning the node 324b within the recovery fluid 308 stream allows the largest particles 326 to be carried out of the chip 316 with the recovery fluid 308, separating them from other sample components that remain in the sample 212 stream. In one embodiment a second fluid channel ("bypass channel 304") is located substantially parallel to the separation channel. A wall 322 that is thin enough to negligibly effect the transmission of ultrasound between the bypass and separation channel ("acoustically transparent wall 322") is located between the two channels. In another embodiment the stream of concentrated particles is positioned off-center in the fluid channel by means of a gel positioned adjacent the fluid channel.

The present invention enables improved operation of the acoustic separation module within the context of a Microfluidic Sample Preparation Platform that aims to purify, separate, and fractionate different classes of particles (mammalian and bacterial cells, nucleic adds, viruses, etc.) from complex biological samples for both clinical (blood, wine, saliva, etc.)

and environmental analysis (food, water, aerosol, etc.). These analyses have obvious applications in areas such as biothreat detection, pathogen identification, epidemic monitoring, virology, and vaccine production, among others. The present invention can be used on its own or in conjunction with other sample processing steps to prepare biological samples before they are introduced into a great variety of commercial instruments for manipulating or analyzing biological samples, such as DNA sequencing, PCR, flow cytometry, microorganism detection, etc.

The embodiment illustrated in FIG. 3A is designated generally by the reference numeral 300. The device 300 has an "H-filter" geometry in which two fluids are pumped side-by-side down a microfluidic separation channel with two inlets and two outlets. One of the two fluids is the sample 312, and the other fluid is a "recovery" buffer 308, which is an appropriate medium (water or buffer) into which focused particles are transferred, while the unfocused components remain in the sample and continue straight through the system. Channel depth (typically 100-300 micrometers), width (typ. 300-1000 micrometers), and wall thickness (typ. 10-40 micrometers) are determined for each chip based on the desired acoustic pressure fields, and fabricated by means of standard photolithography with anisotropic etching. The two fluids enter the separation channel through separate inlets, and the separated sample fractions are collected at the two outlets.

The present invention provides an ultrasonic microfluidic apparatus for separating small particles 318 from large particles 326 contained in the sample fluid 312. A sample input channel 310 is provided for conveying the sample fluid 312 containing small particles 318 and large particles 326 toward the separation area. A recovery fluid input channel 306 containing recovery fluid 308 is muted to convey the recovery fluid substantially parallel and adjacent the sample fluid. Within the separation channel, the recovery fluid 308 contacts the sample fluid 312. A bypass fluid channel 302 containing bypass fluid 304 is located substantially parallel and adjacent the separation channel. An acoustically transparent wall 322 is located between the bypass channel 302 and the separation channel. The bypass channel 302 together with the wall 322 comprise an acoustic extension structure.

An acoustic transducer 314 in contact with the microfluidic chip 316 produces an ultrasound pressure field throughout these fluids. Properly tuned to match the geometric parameters of the channel, the acoustic transducer 314 generates a resonant standing wave within the fluids, creating one or more zones of minimal pressure amplitude (acoustic nodes) toward which particles are driven. The forces that particles experience are dependent on particle size; therefore, the largest particles 326 move toward the node fastest. Positioning the node 324b within the recovery fluid 312 stream allows the largest particles 326 to be carried out of the chip 316 with the recovery fluid 308, separating them from other sample components that remain in the sample 312 stream.

Figure 3B:
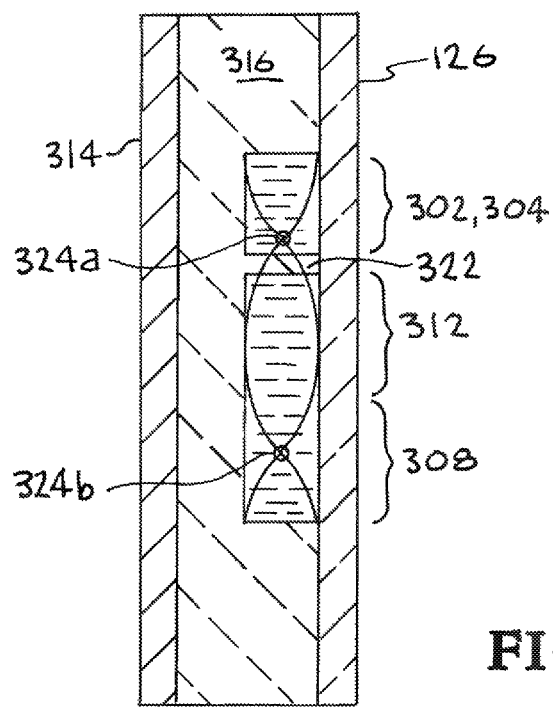

Referring now to FIG. 3B, a cross section taken along lines 3B of FIG. 3A in the direction of the arrows is shown. The body of the chip 316 includes a glass cover plate 126. The body of the chip 316 and the glass cover plate 126 enclose the bypass fluid channel 304, the bypass fluid 302, the recovery fluid 308, and the sample fluid 312. The acoustically transparent wall 322 maintains the bypass fluid 302 separate from the sample fluid 308.

The acoustic transducer 314 produces the two acoustic nodes 324a and 324b such that the first node 32b is located in the recovery fluid 308 stream so that the recovery fluid 308 receives the large particles 326 that are concentrated at the first node 324b causing them to be carried by the recovery fluid 308 out of the "large particle" outlet (LPO) 330. The second node 324a is located in the bypass channel 304, and does not participate in the separation.

Example 3

Alternative Fluid Channel Layout

Figure 4A:
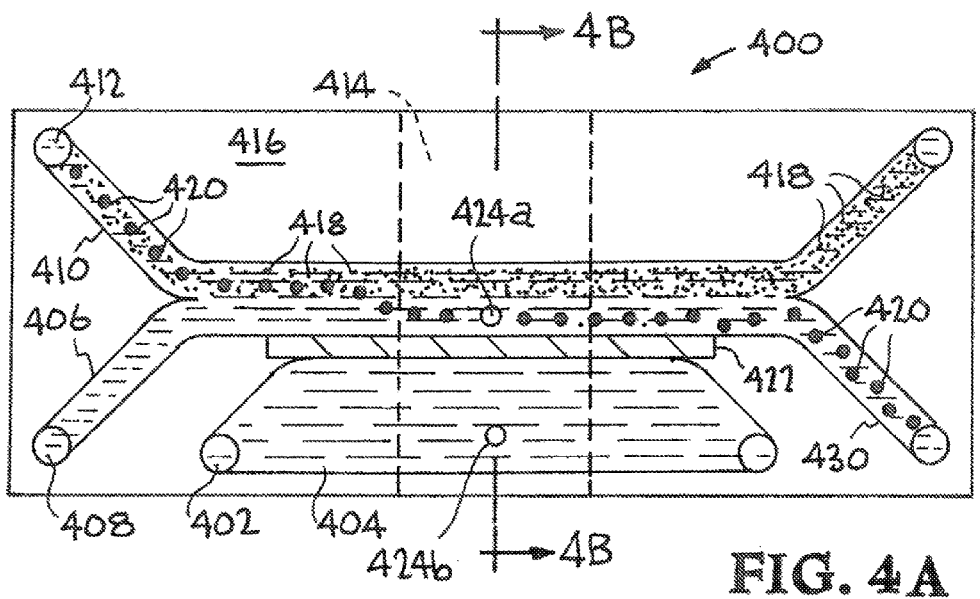
FIGS. 4A and 4B illustrate another embodiment of the invention wherein a transducer produces two nodes, while the separation channel is designed to be narrower than the bypass channel.

Referring now to the drawings and in particular to FIG. 4A, another embodiment of the present invention is illustrated. The device uses multiple microfluidic channels running in parallel along the length of a microfluidic chip, separated by specifically-designed distances (the "wall thickness"). One of these multiple channels serves as the separation channel and has two inlets and two outlets. The ultrasound standing-wave pressure fields are optimized to transfer focused particles out of the sample stream and into the recovery fluid within the recovery fluid channel. The piezoelectric transducer may be driven at single or multiple frequencies to achieve the optimal node placement depending on the channel and wall geometry. In addition, multiple small piezoelectric transducers may be arranged to produce different sound fields in different regions of the chip.

The embodiment illustrated in FIG. 4A is designated generally by the reference numeral 400. The device 400 has an "H-filter" geometry in which two fluids are pumped side-by-side down a microfluidic separation channel with two inlets and two outlets. One of the two fluids is the sample fluid 412, and the other fluid is a "recovery" buffer 408, which is an appropriate medium (water or buffer) into which focused particles are transferred, while the unfocused components remain in the sample and continue straight through the system. Channel depth (typically 100-300 pm), width (typ. 300-1000 pm), and wall thickness (typ. 10-40 pm) are determined for each chip based on the desired acoustic pressure fields, and fabricated by means of standard photolithography with anisotropic etching. The two fluids enter the separation channel through separate inlets, and the separated sample fractions are collected at the two outlets.

The present invention provides an ultrasonic microfluidic apparatus for separating small particles 418 from large particles 420 contained in the sample fluid 412. A sample input channel 410 is provided for conveying the sample fluid 412 containing small particles 418 and large particles 420 toward the separation area. A recovery fluid input channel 406 containing recovery fluid 408 is routed to convey the recovery fluid substantially parallel and adjacent the sample fluid. Within the separation channel, the recovery fluid 408 contacts the sample fluid 412. A bypass fluid channel 204 containing bypass fluid 204 is located substantially parallel and adjacent the separation channel. Note that the bypass fluid channel is a wide channel compared to the bypass channel shown in the previously described embodiments. An acoustically transparent wall 422 is located between the bypass channel 204 and the separation channel 406. The bypass channel 404 together with the wall 422 comprise an acoustic extension structure.

An acoustic transducer 414 in contact with the microfluidic chip 416 produces an ultrasound pressure field throughout these fluids. Properly tuned to match the geometric parameters of the channel, the acoustic transducer 414 generates a resonant standing wave within the fluid, creating one or more zones of minimal pressure amplitude (acoustic nodes) toward which particles are driven. The forces that particles experience are dependent on particle size; therefore, the largest particles 420 move toward the node 424b fastest. Positioning the node 424b within the recovery fluid 408 stream allows the largest particles 420 to be carried out of the chip 416 with the recovery fluid 408, separating them from other sample components that remain in the sample 412 stream.

Figure 4B:
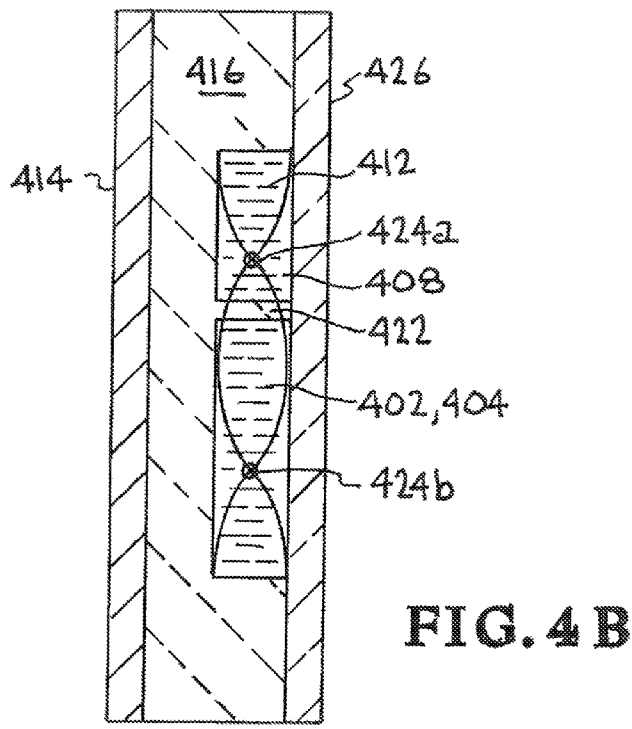

Referring now to FIG. 4B, a cross section taken along lines 4B of FIG. 4A in the direction of the arrows is shown. The body of the chip 416 includes a glass cover plate 426. The body of the chip 416 and the glass cover plate 126 enclose the bypass fluid channel 404, the bypass fluid 402, the recovery fluid 408, and the sample fluid 412. The acoustically transparent wall 422 maintains the bypass fluid 402 separate from the recovery fluid 408.

The acoustic transducer 414 produces the acoustic nodes 424a and 424b. The first node 424a is located in the recovery fluid 408 stream so that the recovery fluid 408 receives the large particles 420 that are concentrated at the first acoustic node 424a causing them to be carried by the recovery fluid 408 out of the "large particle" outlet (LPO) 430. The second node 424b is located in the bypass channel and does not participate in the separation.

Example 4

Use of a Gel to Modify the Separation Channel Geometry

Figure 5A:
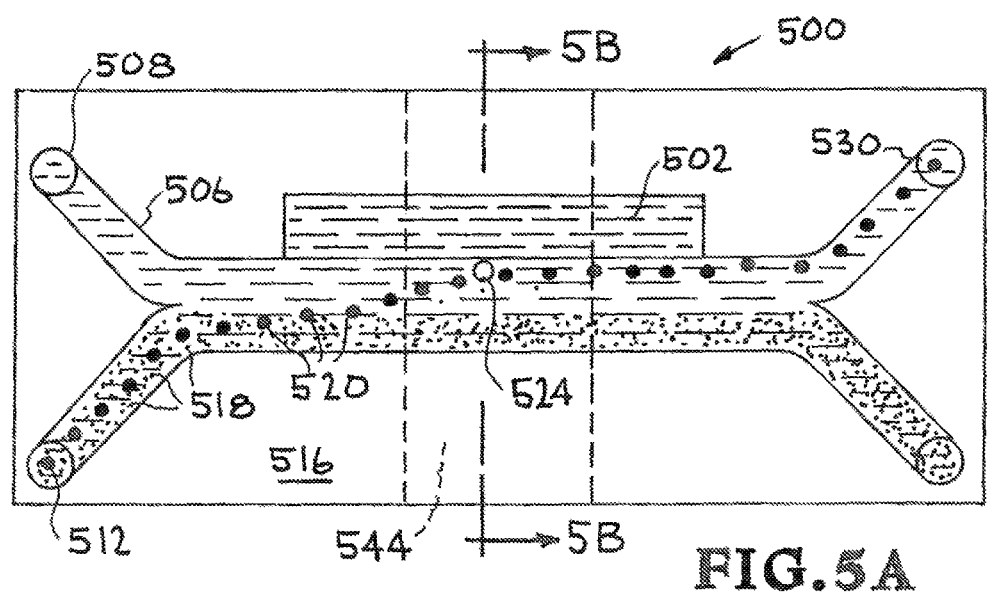
FIGS. 5A and 5B illustrate another embodiment of the invention wherein the stream of concentrated particles is positioned off-center in the fluid channel by means of a gel positioned adjacent the fluid channel.

Referring now to the drawings and in particular to FIG. 5A, another embodiment of the invention is illustrated wherein the stream of concentrated particles is positioned off-center in the fluid channel by means of a region of hydrogel adjacent the fluid channel. In this embodiment, rather than using a second fluid channel separated by a wall, a hydrogel is immobilized (by photopolymerization or by other means) within the searation channel. The ultrasound standing-wave pressure fields are optimized to transfer focused particles out of the sample stream and into the recovery fluid within the recovery fluid channel. The piezoelectric transducer may be driven at single or multiple frequencies to achieve the optimal node placement depending on the channel and wall geometry. In addition, multiple small piezoelectric transducers may be arranged to produce different sound fields in different regions of the chip.

The embodiment illustrated in FIG. 5A is designated generally by the reference numeral 500. The device 500 has an "H-filter" geometry in which two fluids are pumped side-by-side down a microfluidic separation channel with two inlets and two outlets. One of the two fluids, the sample fluid 512, contains the sample and the other fluid is a "recovery" buffer 508, which is an appropriate medium (water or buffer) into which focused particles are transferred, while the unfocused components remain in the sample and continue straight through the system. Channel depth (typically 100-300 micrometers), width (typ. 300-1000 micrometers), and wall thickness (typ. 10-40 micrometers) are determined for each chip based on the desired acoustic pressure fields, and fabricated by means of standard photolithography with anisotropic etching. The two fluids enter the separation channel through separate inlets, and the separated sample fractions are collected at the two outlets.

The present invention provides an ultrasonic microfluidic apparatus for separating small particles 518 from large particles 520 contained in the sample fluid 512. A sample input channel 510 is provided for conveying the sample fluid 512 containing small particles 518 and large particles 520 toward the separation area. A recovery fluid input channel 506 containing recovery fluid 508 is routed to convey the recovery fluid substantially parallel and adjacent the sample fluid. Within the separation channel, the recovery fluid contacts the sample fluid 512. A gel 502 is located substantially parallel and adjacent the separation channel 506. The gel 502 comprises an acoustic extension structure.

An acoustic transducer 514 in contact with the microfluidic chip 516 produces an ultrasound pressure field throughout these fluids. Properly tuned to match the geometric parameters of the channel, the acoustic transducer 514 generates a resonant standing wave within the fluid, creating one or more zones of minimal pressure amplitude (acoustic nodes) toward which particles are driven. The forces that particles experience are dependent on particle size; therefore, the largest particles 420 move toward the node 424 fastest. Positioning the node 524 within the recovery fluid 508 stream allows the largest particles 520 to be carried out of the chip 516 with the recovery fluid 508, separating them from other sample components that remain in the sample stream.

Figure 5B:
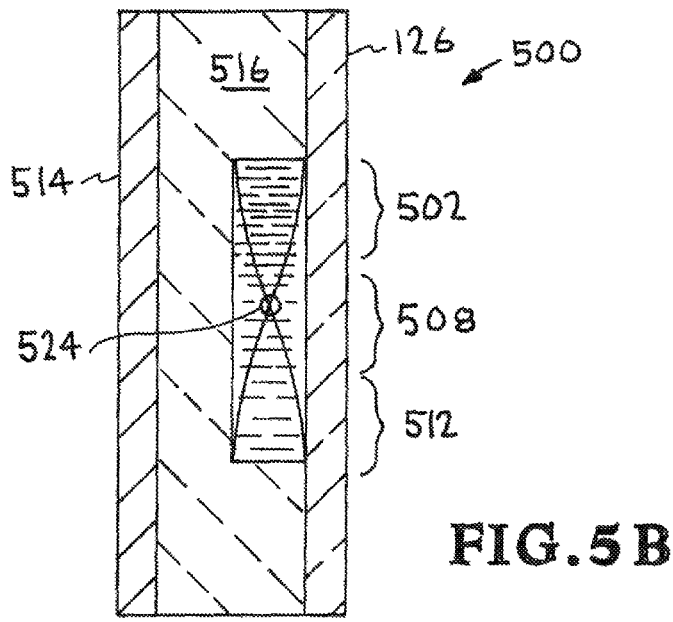

Referring now to FIG. 5B, a cross section taken along lines 5B of FIG. 5A in the direction of the arrows is shown. The body of the chip 516 includes a glass cover plate 126. The body of the chip 516 and the glass cover plate 126 enclose the gel 528, the recovery fluid 508, and the sample fluid 512. The acoustic transducer 514 produces the acoustic node 524 in the recovery fluid stream 506 so that the recovery fluid 508 receives the large particles 520 that are concentrated at the acoustic node 524 causing them to be carried by the recovery fluid 508 out of the "large particle" outlet (LPO) 530.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An ultrasonic microfluidic method for separating small particles from large particles contained in a sample fluid, comprising the steps of:

providing a sample channel for channeling the sample fluid containing the small particles and the large particles;

routing a recovery fluid channel to flow recovery fluid substantially parallel and adjacent said sample fluid, wherein said recovery fluid contacts the sample fluid thereby creating a separation channel;

locating an acoustic extension structure proximate said separation channel, wherein said step of locating an acoustic extension unit proximate said sample channel and said recovery fluid channel comprises locating a bypass fluid channel containing bypass fluid substantially parallel and adjacent said recovery fluid channel and locating an acoustically transparent wall between said bypass channel and said recovery fluid channel wherein said step of locating an acoustic extension unit proximate said sample channel and said recovery fluid channel comprises locating a gel unit proximate said sample channel and said recovery channel positioning said at least one acoustic node off center in said acoustic area concentrating the large particles in said recovery fluid channel; and using an acoustic transducer for producing an ultrasound standing wave that generates a pressure field having at least one node of minimum pressure amplitude, said pressure field encompassing said separation channel, and said acoustic extension structure; wherein said acoustic transducer positions at least one acoustic node off center in said separation channel concentrating the large particles in said recovery fluid stream.

2. An ultrasonic microfluidic method for separating small particles from large particles contained in a sample fluid of, comprising the steps of:
   providing a sample channel for channeling the sample fluid containing the small particles and the large particles;
   routing a recovery fluid channel to flow recovery fluid substantially parallel and adjacent said sample fluid, wherein said recovery fluid contacts the sample fluid thereby creating a separation channel;
   locating an acoustic extension structure proximate said separation channel, wherein said step of locating an acoustic extension unit proximate said sample channel and said recovery fluid channel comprises locating a bypass fluid channel containing bypass fluid substantially parallel and adjacent said recovery fluid channel and locating an acoustically transparent wall between said bypass channel and said recovery fluid channel wherein said step of using an acoustic transducer for producing an acoustic area comprises using an acoustic transducer for producing at least two acoustic nodes that concentrate the large particles in said recovery fluid channel; and
   using an acoustic transducer for producing an ultrasound standing wave that generates a pressure field having at least one node of minimum pressure amplitude, said pressure field encompassing said separation channel, and said acoustic extension structure; wherein said acoustic transducer positions at least one acoustic node off center in said separation channel concentrating the large particles in said recovery fluid stream.

3. An ultrasonic microfluidic method for separating small particles from large particles contained in a sample fluid, comprising the steps of:
   providing a sample fluid stream containing the small particles and the large particles;
   providing a recovery fluid stream located substantially parallel and adjacent to said sample fluid stream, wherein said recovery fluid stream contacts said sample fluid stream;
   providing an acoustic transducer that produces
   an acoustic standing wave, that generates a pressure field having at least one node of minimum sound pressure amplitude; and
      providing an acoustic extension structure located proximate said sample fluid stream and said recovery fluid stream that positions said at least one acoustic node in said
   recovery fluid stream concentrating the large particles in said recovery fluid stream,
   wherein said step of providing an acoustic extension structure located proximate said sample fluid stream and said recovery fluid stream includes providing a gel proximate said recovery fluid stream.

* * * * *